United States Patent
Hörnig

(10) Patent No.: US 9,724,047 B2
(45) Date of Patent: Aug. 8, 2017

(54) MAMMOGRAPHY METHOD AND APPARATUS TO GENERATE AN X-RAY TOMOSYNTHESIS IMAGE OF A BREAST OF A PATIENT

(71) Applicant: Siemens Aktiengesellschaft, Munich (DE)

(72) Inventor: Mathias Hörnig, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 459 days.

(21) Appl. No.: 14/308,776

(22) Filed: Jun. 19, 2014

(65) Prior Publication Data

US 2014/0376691 A1 Dec. 25, 2014

(30) Foreign Application Priority Data

Jun. 19, 2013 (DE) .................. 10 2013 211 547

(51) Int. Cl.
*A61B 6/02* (2006.01)
*A61B 6/00* (2006.01)
(Continued)

(52) U.S. Cl.
CPC .............. *A61B 6/025* (2013.01); *A61B 6/482* (2013.01); *A61B 6/502* (2013.01); *A61B 6/5205* (2013.01);
(Continued)

(58) Field of Classification Search
CPC ......... A61B 6/025; A61B 6/502; A61B 6/482; A61B 6/5205; G06T 11/006; G06T 2211/436
See application file for complete search history.

(56) References Cited

U.S. PATENT DOCUMENTS

2006/0269040 A1\* 11/2006 Mertelmeier .......... A61B 6/502
 378/37
2014/0050302 A1\* 2/2014 Dennerlein ............. G06T 5/001
 378/62

(Continued)

OTHER PUBLICATIONS

"Design of a contrast-enhanced dual-energy tomosynthesis system form breast cancer imaging," Hoernig et al., SPIE Medical Imaging 2012, San Diego.

*Primary Examiner* — Glen Kao
(74) *Attorney, Agent, or Firm* — Schiff Hardin LLP

(57) ABSTRACT

In a mammography method and apparatus to generate a tomosynthetic x-ray image of a breast of a patient, two tomosynthesis scans are successively implemented with different x-ray energies. In one of the scans, a synthetic projection image is generated from at least two projection images acquired in this scan, this synthetic projection image corresponding to a projection at a projection angle at which a projection image has been acquired in the other scan. A difference image, used to reconstruct the tomosynthesis x-ray image, is generated from this synthetic projection image and the projection image acquired in the other scan. Alternatively, in each scan a synthetic projection image is generated from at least two projection images acquired in that scan. Each synthetic projection image represents a projection at the same projection angle. A difference image, used to reconstruct the tomosynthesis x-ray image, is generated from these two synthetic projection images.

21 Claims, 3 Drawing Sheets

(51) Int. Cl.
*G06T 11/00* (2006.01)
*A61B 6/04* (2006.01)
(52) U.S. Cl.
CPC ........... *G06T 11/006* (2013.01); *A61B 6/0414* (2013.01); *G06T 2211/436* (2013.01)

(56) References Cited

U.S. PATENT DOCUMENTS

2016/0086356 A1* 3/2016 Abdurahman ......... A61B 6/032
  382/131
2017/0065241 A1* 3/2017 Hoernig ................. A61B 6/025
  378/21

* cited by examiner

MAMMOGRAPHY METHOD AND APPARATUS TO GENERATE AN X-RAY TOMOSYNTHESIS IMAGE OF A BREAST OF A PATIENT

BACKGROUND OF THE INVENTION

Field of the Invention

The present invention concerns a method to generate a tomosynthetic x-ray image of a breast of a patient, as well as a mammography apparatus operated with such a method.

Description of the Prior Art

Tomosynthesis is an imaging modality in which projection images (projection data sets) of an examination subject are acquired with a digital x-ray detector at a number of different projection directions. By known image reconstruction methods, a three-dimensional image data set can be generated from these digital projection images acquired from different projection directions or projection angles in a limited angle range (for example between −25° and +25° relative of the acquisition area of the x-ray detector), i.e. from the image data representing these projection images, this three-dimensional image data set is compose of a number of slice images that each depict a subject slice oriented parallel to the acquisition area of the x-ray detector. Tomosynthesis is in particularly useful in mammography to generate three-dimensional x-ray images of the breast.

From DE 10 2005 022 543 A1 and from M. D. Hoernig et al., "Design of a contrast-enhanced dual-energy tomosynthesis system for breast cancer imaging", Medical Imaging 2012, Proceedings of the SPIE, Vol. 8313, article id. 831340, a contrast-enhanced digital tomosynthesis method is known in which a contrast agent is intravenously injected into the patient before the data acquisition, which contrast agent propagates in the blood vessels of the breast. A first tomosynthetic scan with a low-energy x-ray beam is subsequently implemented, followed by a second tomosynthetic scan with a high-energy x-ray beam. The energy spectrum of the low-energy x-ray beam is thereby selected so that the contrast agent is practically invisible in the respective projection images obtained in that low-energy scan, while the high-energy x-ray beam is strongly absorbed by the contrast agent (for example iodine). From the tomosynthetic 3D x-ray images or volume data sets that are generated in this way, and by a weighted subtraction, a tomosynthetic difference image is generated from which healthy tissue is largely eliminated, which would impair the ability to detect a tumor or a microcalcification. However, in the known procedure it is disadvantageous that slice images that are already plagued with a loss of information (due to the calculation steps taken within the scope of the tomosynthetic reconstruction, for example the use of spectral filters and the dynamic compression given filtered back-projection) are used for the weighted subtraction.

In order to avoid these disadvantages, it is possible before the tomosynthetic reconstruction, to generate a composite projection image from the projection images acquired at a respective angle position, but acquired at different x-ray energies by a weighted subtraction, and then to reconstruct the tomosynthetic 3D x-ray image from such composite images. However, a problem with such a procedure is that the tomosynthesis scan is implemented during a continuous pivot motion of the x-ray tube, such that the projection angles of the first tomosynthesis scan deviate slightly in practice from the projection angles of the second tomosynthesis scan, due to unavoidable tolerances (mechanism, pulse time, timing of the x-ray detector). This angle deviation is typically approximately 0.2 to 0.6°. Thus, in practice, it is not possible to reliably produce the aforementioned composite image by a subtraction of two images respectively acquired at precisely the same projection angle.

SUMMARY OF THE INVENTION

An object of the invention is to provide a method to generate a tomosynthetic x-ray image of a breast of a patient that is improved relative to the prior art. A further object of the invention to provide a mammography apparatus operated with such a method.

According to the invention, two tomosynthesis scans, respectively with x-ray energies that differ from one another, are implemented in chronological succession, in one of the two tomosynthesis scans a synthetic projection image is generated from at least two projection images acquired in this tomosynthesis scan. This synthetic projection image represents a projection at an identical a projection angle with which a projection image has been acquired in the other tomosynthesis scan. From the synthetic projection image and the other projection image, a difference image is generated that is used for reconstruction of the tomosynthetic x-ray image.

The invention thus largely eliminates the aforementioned disadvantages that conventionally occur with a weighted subtraction in the projection domain, without it being necessary to stop the mammography apparatus that is used to generate the projection images at the individual angle positions and to conduct the acquisitions with different x-ray energies at this stopped position.

In this way it is possible to initially implement a complete tomosynthesis scan with a first x-ray energy with continuous movement of the x-ray tube, followed by a complete tomosynthesis scan implemented with a second x-ray energy. In other words: all first digital projection images can be acquired before or after the acquisition of all second digital projection images.

Is likewise possible to implement one of the two tomosynthesis scans (preferably the tomosynthesis scan implemented with low-energy x-rays) with a reduced number of angle positions in order to lower the dose exposure of the patient in this way without the quality of the diagnosis therefore being reduced, since dose is primarily based on achieving visibility of the injected contrast agent. In other words: it is possible for the first number of first projection images to be smaller than the second number of second projection images.

In the alternative embodiment a synthetic projection image that represents a projection with the same projection angle is generated in each of the tomosynthesis scans from at least two respective projection images acquired in that tomosynthesis scan, and a difference image that is used for reconstruction of the tomosynthetic x-ray image is generated from the two synthetic projection images associated with one another by the angle.

As used herein, a projection image means an image data set of the actual intensities (raw data) measured (detected) point by-point (pixel-by-pixel) by the x-ray detector and that has not yet been subjected to any additional processing steps. An image data set that is created by individual point calculation of the difference of the raw data of two projection images associated with one another is designated in the following as a difference image. The term "synthetic projection image" means an image data set that has been determined by calculation from the image data for a projection angle at which data have been measured (detected) in the acquisition of the projection images, at which synthetic projection angle no real acquisition of a projection image has occurred.

In one embodiment of the method, the synthetic projection image is generated by a weighted addition of projection images adjacent to one another in the same tomosynthesis scan. The synthetic projection image generated in this way then corresponds to an acquisition with a projection angle that lies between the projection angles with which the adjacent projection images have been acquired.

As an alternative to this, the synthetic projection image can be determined by generating a tomosynthetic x-ray image from the projection images generated in a tomosynthesis scan, from which tomosynthetic x-ray image a projection image is then reconstructed by back-projection. For example, such a procedure is known from U.S. Pat. No. 7,760,924 B2. In such a procedure, it would fundamentally be possible to implement the two tomosynthesis scans such that none of the respective projection angles that are used lie near to one another since, through a back-projection, it is possible in principle to reconstruct a projection image associated with an arbitrarily selected projection angle from the respective volume images.

The mammography apparatus according to the invention has an x-ray source that is mounted so as to be pivotable into different angle positions so as to emit x-rays at respective projection angles that differ from one another, and with at least two x-ray energies that differ from one another, as well as an x-ray detector to acquire a projection image at each projection angle. According to the invention a control and evaluation device is provided that executes an algorithm therein so as to implement the method according to the invention as described above.

DESCRIPTION OF THE PREFERRED EMBODIMENTS

Figure 1:
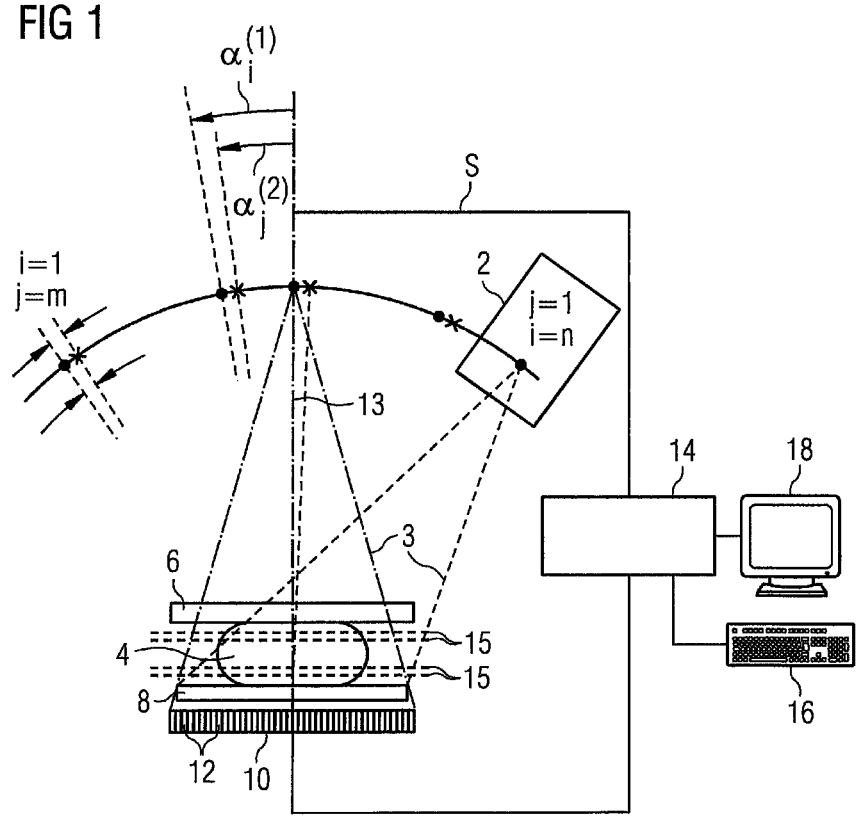
FIG. 1 shows a mammography apparatus according to the invention.

As shown in FIG. 1, the mammography apparatus has an x-ray tube 2 to generate x-rays 3 that traverse the breast 4 of a patient that is embedded between a compression plate 6 and a support plate 8. The x-rays 3 traversing the breast 4, the compression plate 6 and the support plate 8 are received by a large-area digital x-ray detector 10 that is made up of a plurality of individual detectors 12 arranged in a matrix-like array. The x-ray source 2 can move into different first and second angle positions i=1 through n and j=1 through m—in the example it is pivoted—so that first and second projection images $p^{(1)}_i$, $p^{(2)}_j$ of the examination subject 4 can be generated with different first and second projection angles $\alpha^{(1)}_i$, $\alpha^{(2)}_j$ relative to the normal 13 of the support plate 8 of the x-ray detector 10. In FIG. 1, the angle positions of the foci from which the x-rays 3 emanate are respectively drawn for different projection angles.

In the first angle positions i, the x-ray tube 2 emits x-rays 3 with a first x-ray energy $E^{(1)}$, emanating from foci represented by dots in FIG. 1, such that a first number n of first projection images $p^{(1)}_i$ (that are acquired at different projection angles $\alpha^{(i)}_i$) are generated in a first tomosynthesis scan. For this purpose, the x-ray tube 2 is moved or pivoted continuously starting from the angle position i=1—up to an angle position i=n (corresponding to an end position), with an x-ray pulse having triggered in each of these first angle positions i.

A contrast agent is injected into the patient either before the first tomosynthesis scan and before the second tomosynthesis scan, or between the first and second tomosynthesis scan.

In the presented example, a second tomosynthesis scan subsequently takes place in the opposite direction for a second number m of second angle positions j, wherein in this second tomosynthesis scan the acquisition of the second projection images $P^{(2)}_j$ takes place with a second x-ray energy $E^{(2)}$, emanating from foci represented by crosses. In this case as well, the x-ray tube 3 is pivoted continuously—starting from the angle position j=1 up to an end position j=m—and an x-ray pulse is triggered in each of these second angle positions j.

The points in time in which the x-rays 3 are respectively triggered given continuous movement of the x-ray tube 2 are thereby selected so that—depending on whether the first number n is smaller than or greater than the second number m—either a second projection angle $\alpha^{(2)}_j$ is associated with each first projection angle $\alpha^{(1)}_i$, or a first projection angle $\alpha^{(1)}_i$ is associated with each second projection angle $\alpha^{(2)}_j$, which projection angles are situated as close together as possible with allowable technical effort. In practice, however, it has been shown that deviations of up to approximately 0.6° must be accepted. In other words: the acquisitions of the first and second projection images $P^{(1)}_i$, $P^{(2)}_j$ associated with one another take place in the same desired position, but from different real positions due to unavoidable tolerances, meaning that they are acquired from the actual existing first or second angle positions i, j. In this way, the first and second projection angles $\alpha^{(1)}_i$, $\alpha^{(2)}_j$ that are associated with the same desired position but correspond to different real positions (and are accordingly associated with one another) form a projection angle pair.

First and second angle positions n, m normally coincide. However, it is possible in principle to implement one of the two tomosynthesis scans with a reduced number of exposures. However, in contrast-enhanced tomosynthesis—in which the first x-ray energy $E^{(1)}$ is less than the second x-ray energy $E^{(2)}$—the first number n can be smaller than the second number m to reduce the entire dose that is applied in the two tomosynthesis scans.

The actual projection angles $\alpha^{(1)}_i$, $\alpha^{(2)}_j$ (real positions) that are present upon triggering the x-ray radiation are either known in advance (via prior calibration) for the respective mammography apparatus or are respectively detected with a path or angle sensor at the point in time of the triggering of the x-rays.

In the example, a mammography apparatus is shown with x-ray tube 2 arranged so that it may pivot. In principle, it is also possible to acquire projection images from different projection directions with an x-ray tube borne so that it may be displaced linearly on a rail and may pivot around a pivot axis oriented orthogonal to this rail.

The control of the first and second angle positions i, j in which the x-ray tube 2 is triggered, as well as the control of their operating parameters, takes place via control signals S that are generated by a control and evaluation device 14. With the use of input and display elements (symbolically illustrated via a keyboard 16 and a monitor 18), various method variants that are explained in the following can be selected and implemented by the user.

The first and second projection images $P^{(1)}$, $P^{(2)}$ that are generated in this way are processed in the control and evaluation device 14 via procedures (depending on selected method variants) explained in detail in the following and are assembled via reconstruction into a contrast-enhanced, tomosynthetic 3D x-ray image T that includes a number of slice images that render different subject planes 15 parallel to the support plate 8.

Figure 2:
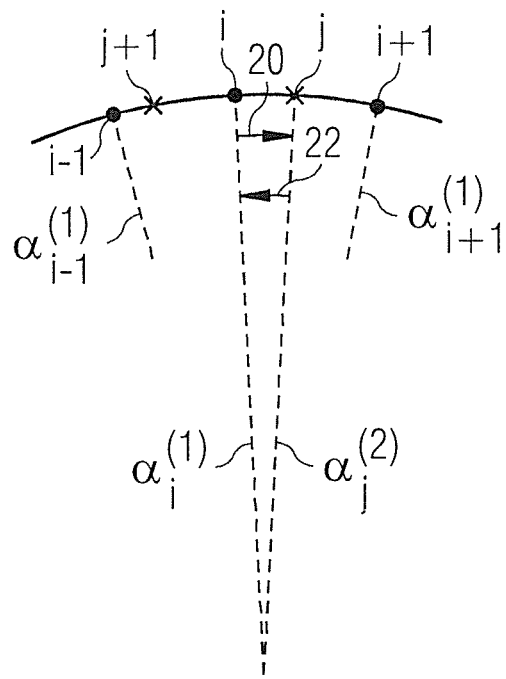
FIGS. 2 and 3 are respective simplified depictions showing the different procedures in the generation of the synthetic projection image or synthetic projection images.
Figure 3:
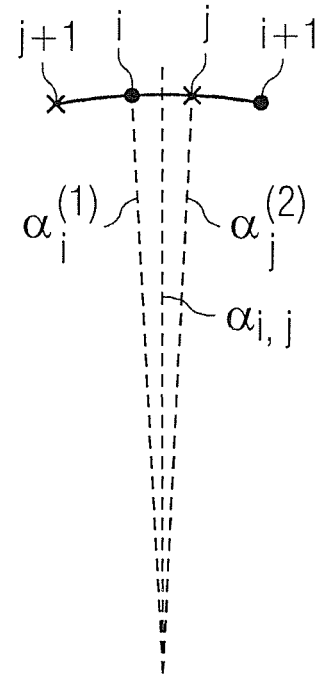

The different method variants are illustrated in FIGS. 2 and 3.

Two first and second angle positions i, j that are situated close together (i.e. are associated with the same desired position) as well as the associated projection angles $\alpha^{(1)}_i$, $\alpha^{(2)}_j$ of a projection angle pair are presented in FIG. 2. Now, either the first projection image $P^{(1)}_i$ that is generated at the first projection angle $\alpha^{(1)}_i$ is replaced by a synthetic first projection image $SP^{(1)}_i$ that corresponds to a projection with a second projection angle $\alpha^{(2)}_j$ that is associated with the first projection angle $\alpha^{(1)}_i$ (arrow 20), or the second projection image $P^{(2)}_j$ that is generated at the second projection angle $\alpha^{(2)}_j$ is replaced by a synthetic second projection image $SP^{(2)}_j$ that corresponds to a projection with a first projection angle $\alpha^{(1)}_i$ that is associated with the second projection angle $\alpha^{(2)}_j$ (arrow 22).

In other words: one of the two projection images $P^{(1)}_i$, $P^{(2)}_j$ that are associated with one another and acquired from different adjacent projection angles $\alpha^{(1)}_i$, $\alpha^{(2)}_j$ is replaced with a synthetic projection image $SP^{(1)}_i$ or $SP^{(2)}_j$ that corresponds to a projection with a projection angle $\alpha^{(2)}_j$ or $\alpha^{(1)}_i$ with which the other of the two projection images $P^{(2)}_j$ or $P^{(1)}_i$ has been acquired.

A difference image $DP_{i,k}$ is subsequently generated from the synthetic projection image $SP^{(1)}_i$ and the other projection image $P^{(2)}_j$, which difference image $DP_{i,k}$ is used to reconstruct the tomosynthetic x-ray image T.

First or second synthetic projection images $SP^{(1)}_i$ or $SP^{(2)}_j$ are respectively generated from first or second projection images $P^{(1)}_i$ or $P^{(2)}_j$. For example, this can take place via a weighted addition of the first or second projection images $P^{(1)}_i$, $P^{(1)}_{i+1}$ or $P^{(2)}_j$, $P^{(2)}_{j+1}$ (which are adjacent to one another and acquired with the same x-ray energy $E^{(1)}$ or $E^{(2)}$, i.e. in the same tomosynthesis scan) between which lies the second or the first projection angle $\alpha^{(2)}_j$ or $\alpha^{(1)}_i$. In this weighted addition, the projection image $P^{(1)}_i$ or $P^{(2)}_j$ that is respectively generated at the angle position i or j that is closer to the second or first angle position j or i is more strongly weighted than the projection image $P^{(1)}_{i+1}$ or $P^{(2)}_{j+1}$ that is respectively generated at the further distant angle position i+1 or j+1.

As an alternative to such a weighted addition of adjacent first or second projection images $P^{(1)}_i$, $P^{(1)}_{i+1}$ or $P^{(2)}_j$, $P^{(2)}_{j+1}$, first or second synthetic projection images $SP^{(1)}$, or $SP^{(2)}_j$ can also be generated in that a tomosynthetic output x-ray image is respectively formed from the first or second projection images $P^{(1)}_i$ or $P^{(2)}_j$, from which tomosynthetic output x-ray image the first or second synthetic projection images $SP^{(1)}_i$ or $SP^{(2)}_j$ are calculated via back-projection. A difference image $DP_{i,k}$ that is used to reconstruct the tomosynthetic x-ray image T is subsequently generated from all present synthetic projection images $SP^{(1)}_i$, $SP^{(2)}_j$ and the respective other projection image $P^{(1)}_i$ or $P^{(2)}_j$.

In the procedure explained using FIG. 3, first and second projection images $P^{(1)}_i$, $P^{(2)}_j$ respectively generated at the first and second projection angles $\alpha^{(2)}_j$, $\alpha^{(1)}_i$ situated close together are replaced by first and second synthetic projection images $SP^{(1)}_i$ or $SP^{(2)}_j$ that correspond to a projection with an intermediate angle $\alpha_{i,j}$ respectively formed from the first projection angles $\alpha^{(1)}_i$ and the second projection angle $\alpha^{(2)}_j$ of a projection angle pair.

In this case, the first and second synthetic projection images $SP^{(1)}_i$, $SP^{(2)}_j$ are also respectively generated from first or second projection images $P^{(1)}_i$ or $P^{(2)}_j$. For example, this can likewise take place via weighted addition of respective adjacent first or second projection images $P^{(1)}_i$, $P^{(2)}_j$ that were acquired at projection angles between which the intermediate angle $\alpha_{i,j}$ is located. In other words: a synthetic projection image $SP^{(1)}_i$, $SP^{(2)}_j$ is respectively generated from projection images $P^{(1)}_i$, $P^{(2)}_j$ that are associated with one another and were acquired from different adjacent projection angles $\alpha^{(1)}_i$, $\alpha^{(2)}_j$, which synthetic projection image $SP^{(1)}_i$, $SP^{(2)}_j$ corresponds to a projection with the same projection angle or intermediate angle $\alpha_{i,j}$ that is located between the associated projection angles $\alpha^{(1)}_i$, $\alpha^{(2)}_j$ that are situated close together.

As an alternative to this, in this procedure it is also possible to calculate the synthetic projection images $SP^{(1)}_i$, $SP^{(2)}_j$ via back-projection from previously generated tomosynthetic output x-ray images.

Figure 4:
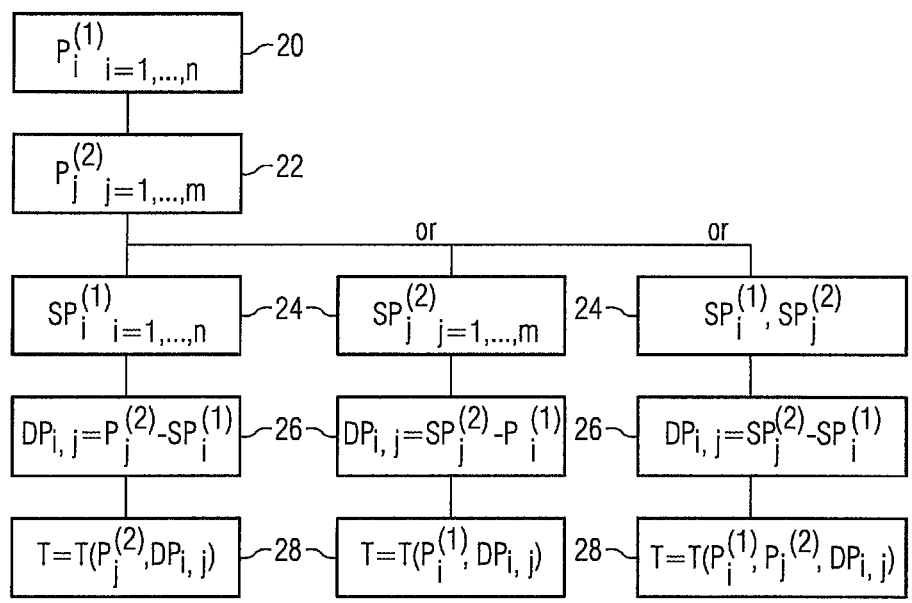
FIG. 4 is a flowchart illustrating different embodiments of the method according to the invention.

The procedures illustrated in FIGS. 2 and 3 are presented in detail in the flow diagram according to FIG. 4, using Steps 20 through 28.

In Step 20, a first tomosynthesis scan is implemented during a continuous movement of the x-ray tube (a pivot movement in the example of FIG. 1), in which a first number n of first projection images $P^{(1)}_i$ acquired with a first x-ray energy $E^{(1)}$ with different first projection angles $\alpha^{(1)}_i$ are generated.

In Step 22, a second tomosynthesis scan is subsequently implemented in which a second number in of second projection images $P^{(2)}_j$ acquired with a second x-ray energy $E^{(2)}$ with different second projection angles $\alpha^{(2)}_j$ are generated, wherein either each first projection angle $\alpha^{(1)}_i$ is respectively associated with a second projection angle $\alpha^{(2)}_j$ that is different than said first projection angle $\alpha^{(1)}_i$, or each second projection angle $\alpha^{(2)}_j$ is respectively associated with a first projection angle $\alpha^{(1)}_i$ that is different than said second projection angle $\alpha^{(2)}_j$, such that first and associated second projection angles $\alpha^{(1)}_i$, $\alpha^{(2)}_j$ or second and associated first projection angles $\alpha^{(2)}_j$, $\alpha^{(1)}_i$ form a projection angle pair.

The first or second images $P^{(1)}_i$, $P^{(2)}_j$ that are associated with one another are either replaced by a number of first synthetic or second synthetic projection images $SP^{(1)}_i$, $SP^{(2)}_j$ that correspond to the first number n (as this is shown to the left in Step 24) or the second number m (as this is shown in the middle in Step 24), wherein the first synthetic projection image $SP^{(1)}_i$ corresponds to a projection with the second projection angle $\alpha^{(2)}_j$ respectively associated with the first projection angle $\alpha^{(1)}_i$ or the second synthetic projection image $SP^{(2)}$ corresponds to a projection with the first projection angle $\alpha^{(1)}_j$ respectively associated with the second projection angle $\alpha^{(2)}_j$.

In Step 26, for each projection angle pair a difference image $DP_{i,j}$ is generated from the first or second synthetic projection image $SP^{(1)}_i$, $SP^{(2)}_j$ and the associated second or first projection image $P^{(1)}_i$, $P^{(2)}_j$. The tomosynthesis x-ray image T is then reconstructed from the projection images $DP_{i,j}$ assembled in this way and the possibly present first or second projection images $P^{(1)}_i$, $P^{(2)}_j$ that are not associated with a projection angle pair.

As an alternative to the procedure explained in detail to the left and in the middle of FIG. 4, in Step 24 shown to the right, either a number (corresponding to the first number n or the second number m) of first synthetic and second synthetic projection images $SP^{(1)}_i$, $SP^{(2)}_j$ are generated from the first or second projection images $P^{(1)}_i$, $P^{(2)}_j$, wherein first and second synthetic projection images $SP^{(1)}_i$, $SP^{(2)}_j$ correspond to a projection with a projection angle $\alpha_{i,j}$ respectively formed from the first projection angle and the second projection angle $\alpha^{(1)}_i$, $\alpha^{(2)}_j$ of a projection angle pair. For each projection angle pair, a difference image $DP_{i,j}$ is subsequently generated in Step 26 from the first synthetic projection image and the second synthetic projection image $SP^{(1)}_i$ or $SP^{(2)}_j$. In Step 28, the tomosynthesis x-ray image T is subsequently formed from the difference images $DP_{i,j}$ and the possibly present first or second projection images $P^{(1)}_i$, $P^{(2)}_j$ that are not associated with a projection angle pair.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method to generate an x-ray tomosynthesis image of a breast of a patient comprising:
   operating an x-ray imaging apparatus to conduct two tomosynthesis scans in a chronological succession, each comprised of a plurality of projection images acquired at respective projection angles, with said x-ray imaging apparatus being operated at x-ray energies that differ from each other respectively in said two tomosynthesis scans;
   providing the projection images acquired in each of said two tomosynthesis scans to a computerized processor and, in said processor, for one of said two tomosynthesis scans, generating a synthetic projection image from at least two projection images acquired in said one of said two tomosynthesis scans, said synthetic projection image being a projection image at a projection angle that corresponds to a projection angle of one of the projection images acquired in the other of said two tomosynthesis scans;
   in said processor, subtracting said synthetic projection image and said one of said projection images from the other of said two tomosynthesis scans, to produce a difference image;
   in said processor, reconstructing an x-ray tomosynthesis image using said difference image; and
   making the x-ray tomosynthesis image available in electronic form at an output of said processor.

2. A method as claimed in claim 1, comprising:
   operating said x-ray imaging apparatus to implement said two tomosynthesis scans by generating a first number of first projection images acquired with a first x-ray energy at respectively different first projection angles, and to generate a second number of second projection images acquired with a second x-ray energy at respectively different second projection angles;
   in said processor, pairing respective first and second projection angles to form respective projection angle pairs by pairing either a first projection angle with a second projection angle that is different from that first projection angle, or by pairing a second projection angle with a first projection angle that is different from that second projection angle;
   in said processor, generating a number, equal to said first plurality, of synthetic projection images, each synthetic projection image being formed from two adjacent first projection images, but at a projection angle equal to the projection angle of a second projection angle paired with the respective projection angle of one of said two adjacent first projection images, and replacing said one of said first projection images with the synthetic projection image formed therefrom;
   in said processor, forming a difference image between each synthetic projection image and the second projection image at the projection angle paired with the projection angle of said one of said two adjacent first projection images, thereby obtaining a plurality of difference images; and
   in said processor, reconstructing said x-ray tomosynthesis image from said plurality of difference images and any of said second projection images that were not used to form one of said difference images.

3. A method as claimed in claim 2 comprising operating said x-ray imaging apparatus with said first x-ray energy being lower than said second x-ray energy.

4. A method as claimed in claim 1, comprising:
   operating said x-ray imaging apparatus to implement said two tomosynthesis scans by generating a first number of first projection images acquired with a first x-ray energy at respectively different first projection angles, and to generate a second number of second projection images acquired with a second x-ray energy at respectively different second projection angles;
   in said processor, pairing respective first and second projection angles to form respective projection angle pairs by pairing either a first projection angle with a second projection angle that is different from that first projection angle, or by pairing a second projection angle with a first projection angle that is different from that second projection angle;
   in said processor, generating a number, equal to said second plurality, of synthetic projection images, each synthetic projection image being formed from two adjacent second projection images, but at a projection angle equal to the projection angle of a first projection angle paired with the respective projection angle of one of said two adjacent second projection images, and replacing said one of said second projection images with the synthetic projection image formed therefrom;
   in said processor, forming a difference image between each synthetic projection image and the first projection image at the projection angle paired with the projection angle of said one of said two adjacent second projection images, thereby obtaining a plurality of difference images; and
   in said processor, reconstructing said x-ray tomosynthesis image from said plurality of difference images and any of said first projection images that were not used to form one of said difference images.

5. A method as claimed in claim 1 comprising generating said synthetic projection image as a weighted addition of respective projection images that are adjacent to each other in said one of said two tomosynthesis scans.

6. A method as claimed in claim 1 comprising, in said processor, generating an x-ray tomosynthesis image from the projection images in said one of said two tomosynthesis scans, and generating said synthetic projection image as a back-projection from said tomosynthesis x-ray image reconstructed from said one of said two tomosynthesis scans, at the projection angle of said projection image acquired in the other of said two tomosynthesis scans.

7. A method as claimed in claim 1 comprising generating said difference image by a weighted subtraction.

8. A method as claimed in claim 1 comprising operating said x-ray imaging apparatus to acquire all of said first projection images either before or after acquiring all of said second projection images.

9. A method as claimed in claim 1 comprising subjecting image data of the respective projection images to no image processing other than generating said synthetic projection image, said difference image and said x-ray tomosynthesis image.

10. A method as claimed in claim 1 comprising operating said x-ray imaging apparatus with contrast agent injected into the patient before acquisition of said first and second projection images.

11. A method to generate an x-ray tomosynthesis image of a breast of a patient comprising:
- operating an x-ray imaging apparatus to conduct two tomosynthesis scans in a chronological succession, each comprised of a plurality of plurality of projection images acquired at respective projection angles, with said x-ray imaging apparatus being operated at x-ray energies that differ from each other respectively in said two tomosynthesis scans;
- providing the projection images acquired in each of said two tomosynthesis scans to a computerized processor and, in said processor, for each of said two tomosynthesis scans, generating a synthetic projection image from at least two projection images acquired in that respective tomosynthesis scan, each synthetic projection image being a projection image at a same projection angle;
- in said processor, subtracting said synthetic projection images, to produce a difference image;
- in said processor, reconstructing an x-ray tomosynthesis image using said difference image; and
- making the x-ray tomosynthesis image available in electronic form at an output of said processor.

12. A method as claimed in claim 11, comprising:
- operating said x-ray imaging apparatus to implement said two tomosynthesis scans by generating a first number of first projection images acquired with a first x-ray energy at respectively different first projection angles, and to generate a second number of second projection images acquired with a second x-ray energy at respectively different second projection angles;
- in said processor, pairing respective first and second projection angles to form respective projection angle pairs by pairing either a first projection angle with a second projection angle that is different from that first projection angle, or by pairing a second projection angle with a first projection angle that is different from that second projection angle;
- in said processor, generating a number, equal to said first plurality, of first synthetic projection images, each synthetic projection image being formed from two adjacent first projection images, but at an intermediate projection angle or at a projection angle equal to the projection angle of a second projection angle paired with the respective projection angle of one of said two adjacent first projection images, and replacing said one of said first projection images with the first synthetic projection image formed therefrom;
- in said processor, generating a number, equal to said second plurality, of second synthetic projection images, each synthetic projection image being formed from two adjacent second projection images, but at an intermediate projection angle or at a projection angle equal to the projection angle of a first projection angle paired with the respective projection angle of one of said two adjacent second projection images, and replacing said one of said second projection images with the synthetic projection image formed therefrom;
- in said processor, forming a difference image between each first synthetic projection image and second projection image at the projection angle paired with the projection angle of said one of said two adjacent first and second projection images, thereby obtaining a plurality of difference images; and
- in said processor, reconstructing said x-ray tomosynthesis image from said plurality of difference images and any of said projection images that were not used to form one of said difference images.

13. A method as claimed in claim 12 comprising operating said x-ray imaging apparatus with said first x-ray energy being lower than said second x-ray energy.

14. A method as claimed in claim 11 comprising generating said synthetic projection image as a weighted addition of respective projection images that are adjacent to each other in said one of said two tomosynthesis scans.

15. A method as claimed in claim 11 comprising, in said processor, generating an x-ray tomosynthesis image from the projection images in said one of said two tomosynthesis scans, and generating said synthetic projection image as a back-projection from said tomosynthesis x-ray image reconstructed from said one of said two tomosynthesis scans, at the projection angle of said projection image acquired in the other of said two tomosynthesis scans.

16. A method as claimed in claim 11 comprising generating said difference image by a weighted subtraction.

17. A method as claimed in claim 11 comprising operating said x-ray imaging apparatus to acquire all of said first projection images either before or after acquiring all of said second projection images.

18. A method as claimed in claim 11 comprising subjecting image data of the respective projection images to no image processing other than generating said synthetic projection image, said difference image and said x-ray tomosynthesis image.

19. A method as claimed in claim 11 comprising operating said x-ray imaging apparatus with contrast agent injected into the patient before acquisition of said first and second projection images.

20. A mammography apparatus comprising:
- an x-ray imaging apparatus;
- a control unit configured to operate the x-ray imaging apparatus to conduct two tomosynthesis scans in chronological succession, each comprised of a plurality of projection images acquired at respective projection angles, with said x-ray imaging apparatus being operated at x-ray energies that differ from each other respectively in said two tomosynthesis scans;
- a computerized processor provided with the projection images acquired in each of said two tomosynthesis scans, said computerized processor being configured to generate for one of said two tomosynthesis scans, generating a synthetic projection image from at least two projection images acquired in said one of said two tomosynthesis scans, said synthetic projection image being a projection image at a projection angle that corresponds to a projection angle of one of the projection images acquired in the other of said two tomosynthesis scans;
- said processor being configured to subtract said synthetic projection image and said one of said projection images from the other of said two tomosynthesis scans, to produce a difference image;

said processor being configured to reconstruct an x-ray tomosynthesis image using said difference image; and said processor being configured to make the x-ray tomosynthesis image available in electronic form at an output of said processor.

21. A mammography apparatus comprising:

an x-ray imaging apparatus;

a control unit configured to operate the x-ray imaging apparatus to conduct two tomosynthesis scans in a chronological succession, each comprised of a plurality of projection images acquired at respective projection angles, with said x-ray imaging apparatus being operated at x-ray energies that differ from each other respectively in said two tomosynthesis scans;

a computerized processor provided with the projection images acquired in each of said two tomosynthesis scans, said computerized processor being configured, for each of said two tomosynthesis scans, to generate a synthetic projection image from at least two projection images acquired in that tomosynthesis scan;

said synthetic projection images each being at a same projection angle;

said processor being configured to subtract said synthetic projection images, to produce a difference image;

said processor being configured to reconstruct an x-ray tomosynthesis image using said difference image; and said processor being configured to make the x-ray tomosynthesis image available in electronic form at an output of said processor.

* * * * *